(12) United States Patent
Lindh, Sr. et al.

(10) Patent No.: US 8,216,497 B2
(45) Date of Patent: Jul. 10, 2012

(54) TISSUE HOLDING DEVICES AND METHODS FOR MAKING THE SAME

(75) Inventors: David Lindh, Sr., Flemington, NJ (US);
Jesse G. Nawrocki, Annadale, NJ (US);
John P. Collier, Franklin States, NJ (US)

(73) Assignee: Ethicon, Inc., Somerville, NJ (US)

( * ) Notice: Subject to any disclaimer, the term of this patent is extended or adjusted under 35 U.S.C. 154(b) by 203 days.

(21) Appl. No.: 12/634,071

(22) Filed: Dec. 9, 2009

(65) Prior Publication Data

US 2010/0084780 A1    Apr. 8, 2010

Related U.S. Application Data (62) Division of application No. 11/743,201, filed on May 2, 2007, now Pat. No. 7,850,894.

(60) Provisional application No. 60/798,806, filed on May 4, 2006.

(51) Int. Cl.
| B29C 45/14 | (2006.01) |
| B29C 59/02 | (2006.01) |
| B28B 7/14 | (2006.01) |
| B28B 7/10 | (2006.01) |
| A61B 17/04 | (2006.01) |
| A61L 17/00 | (2006.01) |

(52) U.S. Cl. ........ 264/153; 264/145; 264/163; 264/320; 264/325; 264/334; 606/228; 606/231; 83/405; 83/231

(58) Field of Classification Search .................. None
See application file for complete search history.

(56) References Cited

U.S. PATENT DOCUMENTS

| 3,123,077 A | 3/1964 | Alcamo |
| 3,700,544 A | 10/1972 | Matsui |
| 3,716,058 A | 2/1973 | Tanner, Jr. |
| 3,720,055 A | 3/1973 | De Mestral et al. |
| 3,805,360 A * | 4/1974 | Brede et al. ................. 29/402.19 |
| 3,833,972 A | 9/1974 | Brumlik |
| 3,845,641 A | 11/1974 | Waller |
| 3,981,051 A | 9/1976 | Brumlik |
| 4,052,916 A * | 10/1977 | Feneberg ..................... 76/107.1 |
| 4,069,825 A | 1/1978 | Akiyama |
| 4,311,658 A * | 1/1982 | Nicoll .......................... 264/175 |
| 4,548,202 A | 10/1985 | Duncan |
| 4,719,787 A * | 1/1988 | Ragland, Jr. .................... 72/347 |

(Continued)

FOREIGN PATENT DOCUMENTS

DE    1810800 A1    6/1970

(Continued)

OTHER PUBLICATIONS

Dattilo, P.P. Jr. et al., "Tissue Holding Performance of Knotless Absorbable Sutures", Society for Biomaterials 29th Annual Meeting Transactions (2003) p. 101.

(Continued)

*Primary Examiner* — Jeffrey Wollschlager (57) ABSTRACT

Various methods are provided for forming tissue holding devices having predetermined shapes suitable for use in surgical applications, and devices formed in accordance with such methods are also provided. These methods include press forming methods, and press forming methods in combination with profile punching. Tissue holding devices formed in accordance with such methods include various configurations for a core and a plurality of tissue holding elements extending outwardly from the core.

12 Claims, 13 Drawing Sheets

U.S. PATENT DOCUMENTS

| | | | |
|---|---|---|---|
| 4,880,585 A | 11/1989 | Klimesch et al. | |
| 4,900,605 A | 2/1990 | Thorgersen et al. | |
| 5,269,783 A | 12/1993 | Sander | |
| 5,269,809 A | 12/1993 | Hayhurst et al. | |
| 5,342,376 A | 8/1994 | Ruff | |
| 5,393,475 A | 2/1995 | Murasaki et al. | |
| 5,395,126 A | 3/1995 | Tresslar | |
| 5,931,855 A | 8/1999 | Buncke | |
| 5,964,783 A | 10/1999 | Grafton et al. | |
| 6,241,747 B1 | 6/2001 | Ruff | |
| 6,322,582 B1* | 11/2001 | Richard et al. | 606/226 |
| 6,599,310 B2 | 7/2003 | Leung et al. | |
| 6,776,789 B2 | 8/2004 | Bryant et al. | |
| 6,848,152 B2 | 2/2005 | Genova et al. | |
| 6,991,643 B2* | 1/2006 | Saadat | 606/221 |
| 7,112,214 B2* | 9/2006 | Peterson et al. | 606/220 |
| 7,231,800 B2* | 6/2007 | Kappali | 72/379.2 |
| 7,478,460 B2 | 1/2009 | Gallant et al. | |
| 7,850,894 B2 | 12/2010 | Lindh, Sr. et al. | |
| 7,914,437 B2* | 3/2011 | Gozzi et al. | 600/29 |
| 2003/0001407 A1 | 1/2003 | Hoshikawa et al. | |
| 2003/0041426 A1 | 3/2003 | Genova et al. | |
| 2003/0074023 A1 | 4/2003 | Kaplan et al. | |
| 2003/0149447 A1* | 8/2003 | Morency et al. | 606/228 |
| 2004/0060409 A1 | 4/2004 | Leung et al. | |
| 2004/0060410 A1 | 4/2004 | Leung et al. | |
| 2004/0088003 A1 | 5/2004 | Leung et al. | |
| 2004/0138705 A1 | 7/2004 | Heino et al. | |
| 2004/0193191 A1 | 9/2004 | Starksen et al. | |
| 2005/0075639 A1* | 4/2005 | Lechot | 606/81 |
| 2005/0116374 A1* | 6/2005 | Ogawa et al. | 264/103 |
| 2005/0118388 A1 | 6/2005 | Kingsford | |
| 2005/0246021 A1 | 11/2005 | Ringeisen et al. | |
| 2005/0260398 A1 | 11/2005 | Owens | |
| 2007/0187861 A1 | 8/2007 | Genova et al. | |

FOREIGN PATENT DOCUMENTS

| | | |
|---|---|---|
| EP | 0204931 A | 12/1986 |
| EP | 0464480 A | 1/1992 |
| EP | 0795336 A | 9/1997 |
| EP | 1457214 | 9/2004 |
| EP | 1429664 B1 | 3/2007 |
| GB | 0191282 | 11/1967 |
| WO | WO 96/06565 A1 | 3/1996 |
| WO | WO 99/01071 A | 1/1999 |
| WO | WO 99/49792 A | 10/1999 |
| WO | WO 03/017850 A2 | 3/2003 |
| WO | WO 2004/030520 A2 | 4/2004 |
| WO | WO 2004/030704 A2 | 4/2004 |
| WO | WO 2004/030705 A2 | 4/2004 |
| WO | WO 2006/005144 A1 | 1/2006 |
| WO | WO 2006/061868 A | 6/2006 |

OTHER PUBLICATIONS

Mc Kenzie, A.R. "An Experimental Multiple Barbed Suture for the Long Flexor Tendons of the Palm and Fingers", The Journal of Bone and Joint Surgery, (1967) vol. 49B, No. 3, pp. 440-447.

Schmid, A. et al., The outspreading anchor cord. A material for arthroscopic suturing of a fresh anterior cruciate ligament rupture.

* cited by examiner

TISSUE HOLDING DEVICES AND METHODS FOR MAKING THE SAME

CROSS-REFERENCE TO RELATED APPLICATION

This application is a divisional of U.S. patent application Ser. No. 11/743,201, filed on May 2, 2007, now U.S. Pat. No. 7,850,894 which claims the benefit of U.S. Provisional Application Ser. No. 60/798,806 filed on May 4, 2006.

BACKGROUND OF THE INVENTION

1. Field of the Invention

The present invention relates to tissue holding devices, and more particularly to tissue holding devices and methods for making the same that are particularly suited for tissue reinforcement, approximation and/or repositioning, or for securing tissue to implantable prostheses.

2. Background Discussion

Sutures have been used for many decades for wound closure and/or tissue approximation in a variety of medical applications. More recently, barbed sutures have been gaining attention for various medical applications as well. Barbed sutures typically have a series of "barbs" that extend outwardly from the suture, with the objective being that such barbs increase the holding strength of the suture and/or eliminate the need for knot tying.

Figure 1:
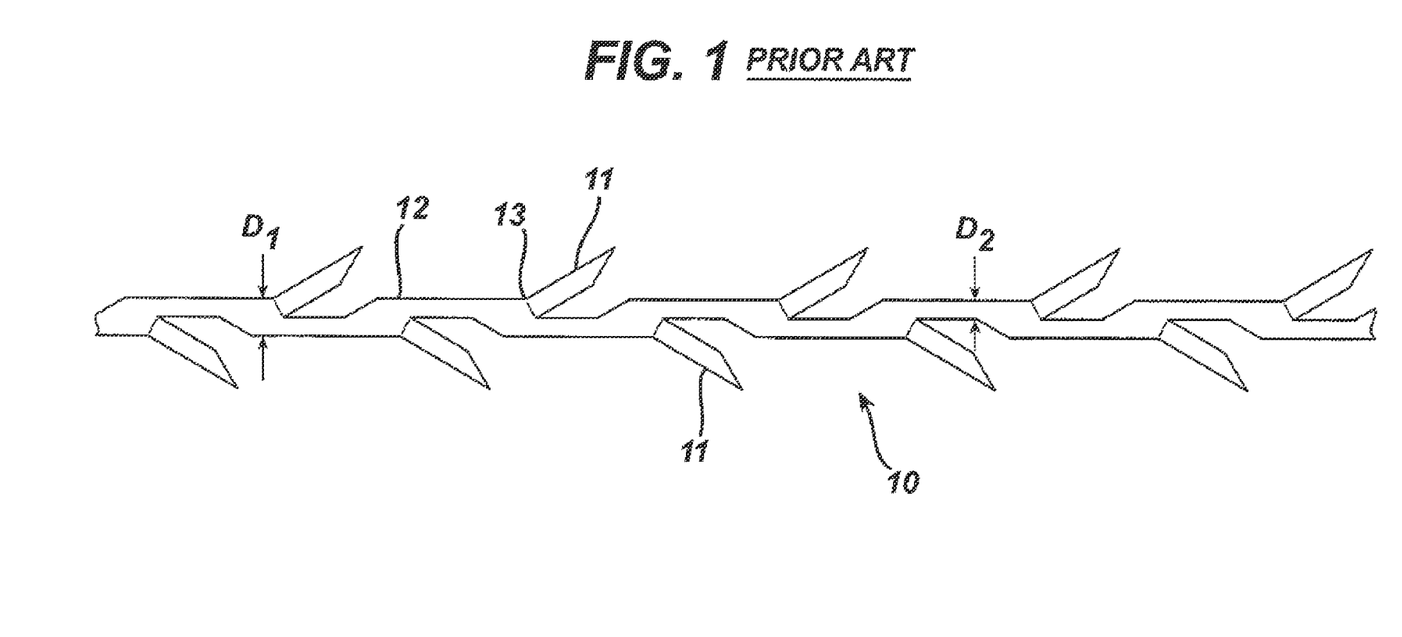
FIG. 1 is a side view of an exemplary prior art suture having barbs cut therein.

In most barbed sutures that exist in the marketplace, the barbs are formed by cutting into the suture shaft with a blade of some sort. An exemplary barbed suture 10 of this type is illustrated in FIG. 1. For each barb 11 that is cut into the suture shaft 12, the end of the cut area, or base 13 of the barb acts as a weak lever that allows the barb to bend backwards under stress. In addition, the diameter of the suture $D_1$ is reduced along the area into which a barb has been cut (as illustrated at $D_2$), which greatly reduces the tensile strength of the suture. Cutting into the suture shaft to form the barbs also has another disadvantage in that the number, size and geometry of the barbs is limited. This is so because the spacing between the barbs, the barb length etc. are greatly constrained by the size of the original suture because the cuts begin to interfere with one another and/or adversely affects the mechanical strength of the suture. There are also size limitations on what can be achieved with such a barbed suture. For example, as the barb size decreases, the size of the tooling necessary to cut the barbs becomes very small and precise, and thus very difficult to manufacture. Further, as the suture diameter decreases, cutting a barb into a very small cross-section decimates the strength of the suture due to the resultant thin core.

Other means for creating suture-like products have been suggested. For example, U.S. Patent Publication No. 2004/0060410 and WO 2006/005144 make reference to other processes such as injection molding, stamping and laser cutting. U.S. Patent Publication No. 2003/0149447 also suggests stamping, progressive die cutting, injection molding, and chemical etching as methods to produce barbed sutures out of a flat material. Each of these suggested methods has its drawbacks. For example, injection molding is a process by which liquid material is injected into a die until the material fills the die, and is then allowed to cool. The sample is subsequently ejected from the die. With this method, however, because the material is first melted to allow for injection into the die, any mechanical strength due to molecular orientation (i.e., such as that seen in a polymer that has been extruded) is mainly lost. Significant thermal treatment such as that experienced in injection molding, decreases the amount of molecular orientation as the chains are able to rearrange into a more random structure. The loss of molecular orientation can adversely affect mechanical properties such as yield strength and bending modulus, which adversely affects the holding strength of the suture. In addition, there is a limitation on the size and shape of the devices that can be made by injection molding. Capillary forces will limit the ability to fill a mold in small areas, long run areas, and intricate geometries. Also, injection molded parts suffer from issues such as warpage and shrinkage.

The publications mentioned above also suggest stamping and die cutting as alternative methods for forming such products. Die cutting is simply the process of cutting shapes from sheets by pressing a shaped knife-edge into one or more layers of sheeting. Stamping is a more general term to denote sheet material press-working. It typically involves impressing a material with some mark or figure. Because these processes only make imprints in, or "cookie cut" shapes in a given material, they cannot be used to create intricate 3-dimensional geometries. Further, die cutting or stamping processes do not promote material flow to fill in a double-female die cavity.

The present invention described herein provides new processes for forming tissue holding devices that overcome the disadvantages of the processes described above. Further, the present invention provides various tissue holding devices having unique geometries achievable using the methods described herein.

SUMMARY OF THE INVENTION

A method is provided for forming a tissue holding device having a predetermined shape suitable for use in surgical applications. The method includes providing a first set of dies each having a top surface having a recess therein sized and shaped such that, when the recesses face and are aligned with one another, a first mold cavity is formed therebetween, providing a polymeric feedstock material, placing the feedstock material between opposing top surfaces of the first set of dies, and with the feedstock material therebetween, pressing the top surfaces of the first set of dies together until substantially in contact with one another so that the feedstock material deforms to fill the first mold cavity formed therebetween to thereby form a pre-form having a shape of the first mold cavity. The method further includes providing a second set of dies each having a top surface having a recess therein sized and shaped such that, when the recesses face and are aligned with one another, a second mold cavity is formed therebetween. The second mold cavity defines the predetermined shape of the tissue holding device. The pre-form is placed between opposing top surfaces of the second set of dies, and with the pre-form therebetween, the method further includes pressing the top surfaces of the second set of dies together until substantially in contact with one another so that the pre-form deforms to fill the second mold cavity formed therebetween to thereby form the tissue holding device having the predetermined shape. The predetermined shape includes a core extending along a length thereof, and a plurality of tissue holding elements extending outwardly therefrom along at least a portion of the length.

In various embodiments the core may have an outermost dimension of less than or equal to 0.02 inches, the plurality of tissue holding elements may have a length less than or equal to 0.2 inches, and/or at least first and second tissue holding elements positioned opposite one another at substantially the same location along the length of the core.

In yet another embodiment, the plurality of tissue holding elements may extend outwardly from the core at an angle, and the tissue holding device may further include a web-like portion extending between an inner side of the tissue holding elements and the core, where the web-like portion is thinner than the tissue holding element.

Also provided is a method for forming a tissue holding device having a predetermined shape suitable for surgical applications, including the steps of providing first and second female dies each having respective first and second top surfaces with first and second recesses formed therein, wherein the first and second recesses are sized and shaped such that, when aligned with one another, they together form a mold cavity defining the predetermined shape. The predetermined shape includes a core extending along a length thereof, and a plurality of tissue holding elements extending outwardly from the core. The method further includes providing a polymeric feedstock material, placing the feedstock material between the top surfaces of the first and second dies, and with the feedstock material therebetween, pressing the top surfaces of the first and second dies together until the top surfaces of the first and second dies are substantially in contact with one another and the recesses of the first and second dies substantially aligned to form the mold cavity, so that the feedstock material deforms and fills the cavity therebetween to thereby form the tissue holding device having the predetermined shape.

Various embodiments may further include a core having an outermost dimension less than or equal to 0.02 inches, a plurality of tissue holding elements having a length less than or equal to 0.2 inches, and/or a plurality of sets of first and second tissue holding elements, wherein for each set the first and second tissue holding elements are positioned substantially opposite one another at substantially the same location along the length of the core.

Also provided are tissue holding devices produced in accordance with the method described above, wherein the core of the tissue holding device has a cross-sectional shape including opposing upper and lower outwardly curved sides and opposing first and second substantially flat lateral sides. The device may further have the plurality of tissue holding elements extending outwardly from the first and/or second lateral sides. In other embodiments of the device, the tissue holding elements may have a length less than or equal to 0.2 inches, and/or the core may have an outmost cross-sectional dimension of less than or equal to 0.02 inches.

In another device produced in accordance with the method described above, at least one of the plurality of tissue holding elements has a web-like portion extending between an inner side of the tissue holding element and the core. In various other devices produced in accordance with the methods described above, the device may include at least one tissue holding element having an inner side having a recess therein, and/or a core having a cross-section that increases in size along at least a portion of the length of the device.

Finally, yet another method is provided for forming a tissue holding device having a predetermined shape suitable for use in surgical applications. The method includes providing a polymeric feedstock material, using a first set of dies, press forming the polymeric feedstock material into a pre-form, and providing a receiver plate and a stripper plate each having a top surface with a recess formed therein having a three-dimensional shaped such that, when the recesses are aligned and facing one another, a cavity is formed therebetween capable of receiving therein the pre-form and having a substantially complementary shape as that of the pre-form. The stripper plate further has a opening therethrough for receiving a punch. The method further includes aligning the receiver and stripper plates and placing the pre-form in the cavity formed therebetween, providing a punch having a punch element having an outer periphery substantially identical to an outer periphery of the predetermined shape of the tissue holding device, and having a three dimensional surface contour substantially complementary to a top surface of a portion of the pre-form to be punched, and pressing the punch element through the top die and into the pre-form to thereby create the tissue holding device of the predetermined shape. The predetermined shape of the tissue holding device includes a core extending along a length thereof, and a plurality of tissue holding elements extending outwardly therefrom along at least a portion of the length.

The pre-form may further have a central portion and first and second enlarged distal ends, with the punch element pressing into only the central portion of the pre-form.

Various tissue holding devices produced in accordance with this method are also provided. Embodiments of such tissue holding devices may further include a core having an outermost cross-sectional dimension of less than or equal to 0.02 inches, the tissue holding elements having a length less than or equal to 0.02 inches, and/or a core having a cross-sectional shape including upper and lower outwardly curved sides and opposing first and second substantially flat lateral sides. In the latter embodiment, the plurality of tissue holding elements may further extend outwardly from the first and/or second lateral sides.

In yet another embodiment, the device further includes a plurality of sets of first and second tissue holding elements, wherein for each set the first and second holding elements are positioned substantially opposite one another at substantially the same location along the length of the core.

In other alternative embodiments, the core may have a substantially uniform cross-section along its length, or may increase in cross-section along at least a portion of its length.

In yet another embodiment, at least one of the plurality of tissue holding elements has an inner side having a recess therein.

Finally, in yet another embodiment, the length of the tissue grasping elements may increases along at least a portion of the length of the tissue holding device.

BRIEF DESCRIPTION OF THE DRAWINGS

FIGS. 7-9b illustrate various configurations of tissue holding devices according to the present invention.

DETAILED DESCRIPTION OF THE INVENTION

Before explaining the present invention in detail, it should be noted that the invention is not limited in its application or use to the details of construction and arrangement of parts illustrated in the accompanying drawings and description. The invention as illustrated may be implemented or incorporated in other embodiments, variations and modifications, and may be practiced or carried out in various ways.

Figure 2A:
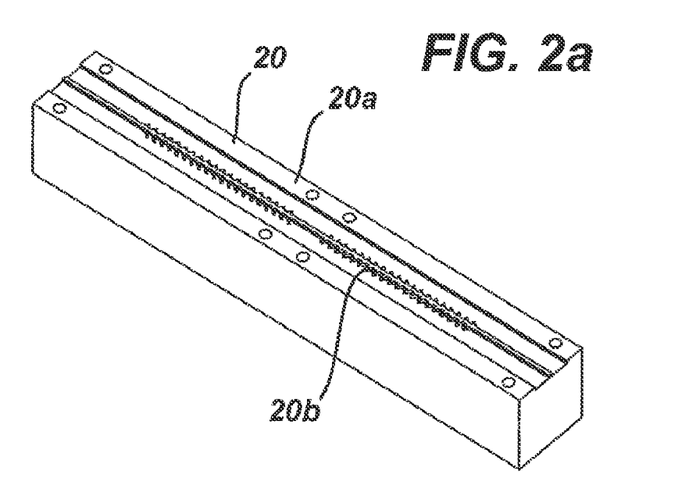
FIGS. 2a-2c illustrate an exemplary die assembly that can be used in connection with the present invention.
Figure 2B:
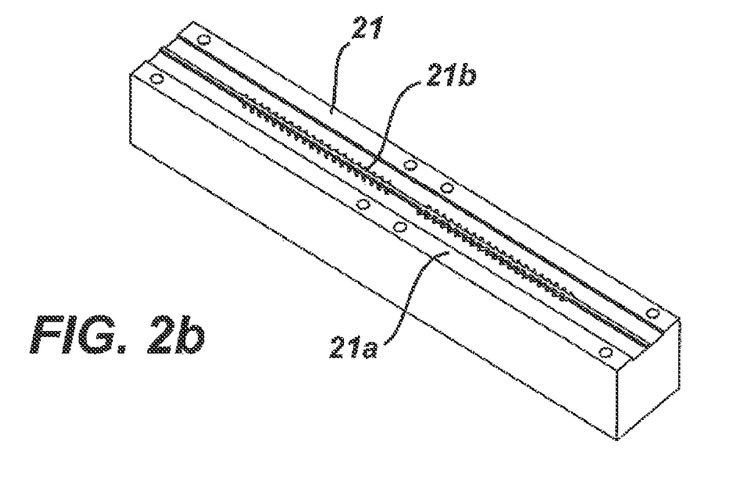
Figure 2C:
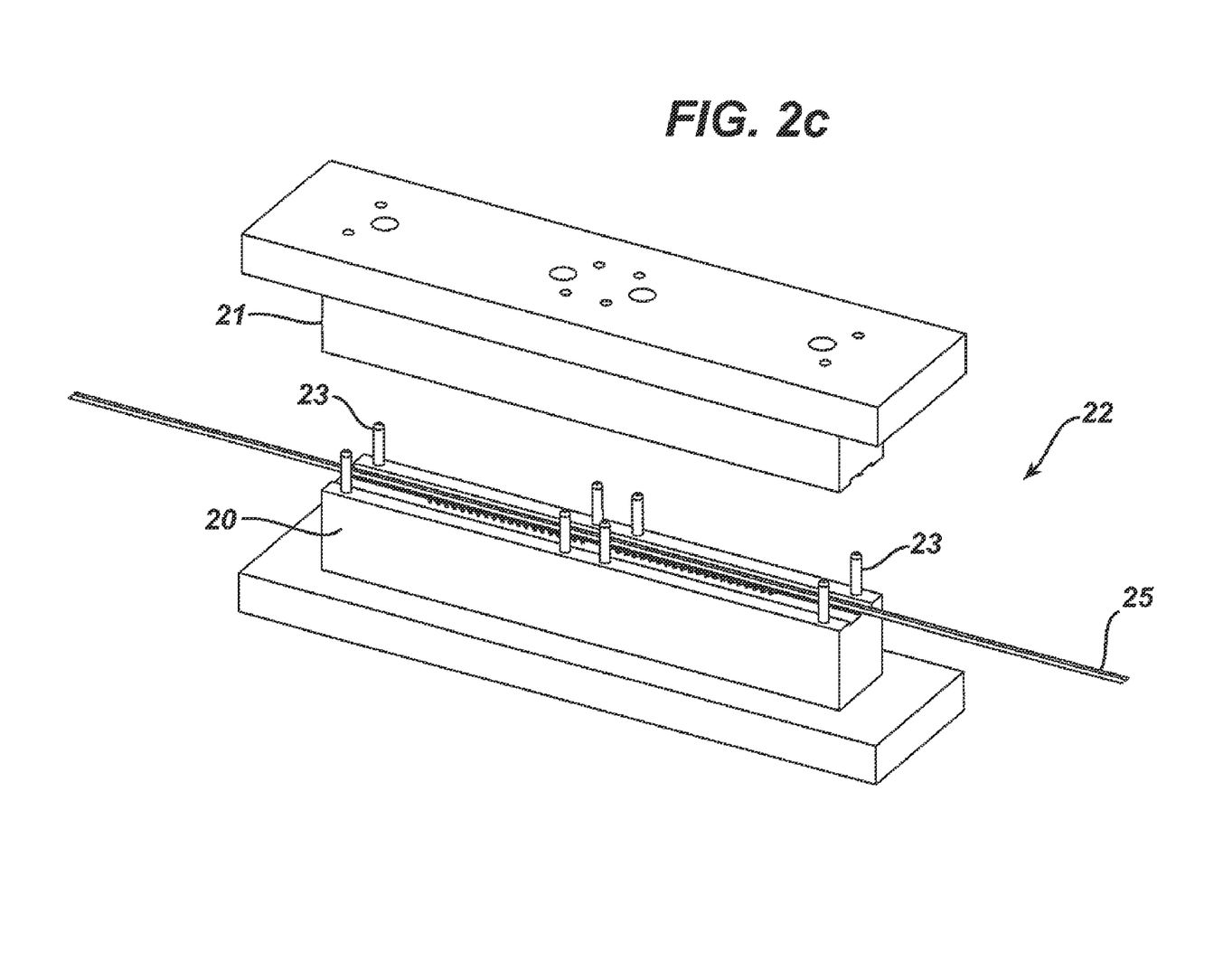

Referring first to FIGS. 2a-c and 3, methods for press forming tissue holding devices according to the present invention will now be described in detail. FIGS. 2a-2c illustrate first 20 and second 21 female dies that together form a die assembly 22 used to form a material into the desired shape using some type of press, such as a hydraulic or pneumatic press or the like. As illustrated in FIGS. 2a and 2b, the top surfaces 20a, 21a of the first and second dies each have a recess 20b, 21b therein having a configuration resembling a portion of the desired tissue holding device to be produced. When the top surfaces are aligned and brought in contact with one another, the recesses together form a cavity or mold in the shape of the desired tissue holding device. The feedstock material, or material to be formed into the tissue holding device, is typically a solid polymeric material having any suitable cross-section, such as circular, elliptical, rectangular, square etc., and having a length necessary for the given application. The material is placed between the first and second dies as shown in FIG. 2c, and the dies closed and forcibly pressed together by a suitable press as described above. Guide pins 23 or the like are typically used to ensure that the proper orientation is maintained between the first and second dies. During the pressing process, the pressure causes material to move into and fill all portions of the die cavities, even any intricate geometries that may exist.

The dies 20, 21 may be compound dies that perform more than one operation in a single stroke of a press. For example, a given set of dies may simultaneously form the tissue holding device and trim excess flash material away by means of pinching, cutting, shearing or the like. The dies and/or the material can be heated to a temperature that aids in material flow, but does not significantly compromise the mechanical properties as occurs with injection molding. In other words, the temperature used will be such that the material softens, but molecular orientation is not completely lost and therefore, the strength and stiffness of the material are not significantly compromised. Softening the material may allow the use of lower pressures during processing and reduce the amount of flash on the finished samples. In fact, some thermal treatments may even improve the "functional" properties of the material. For example, an annealing treatment may be used to relieve stresses and toughen the material.

Figure 3A:
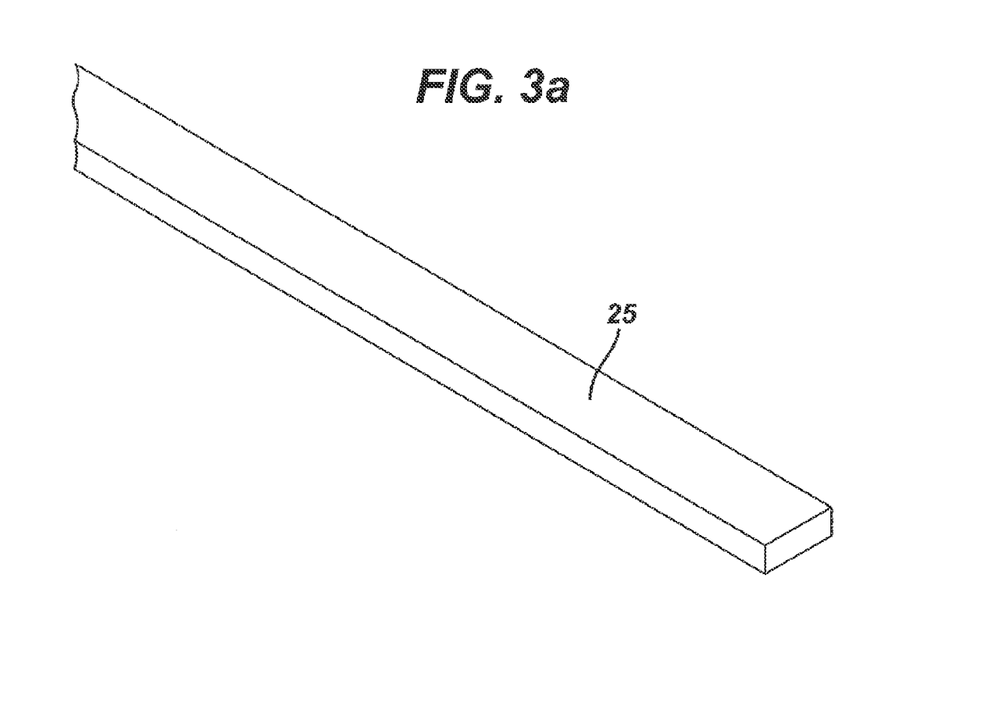
FIGS. 3a-3g illustrate feedstock material at various stages during the formation of a tissue holding device according to exemplary methods of the present invention, and various cross-sectional shapes at such stages.
Figure 3B:
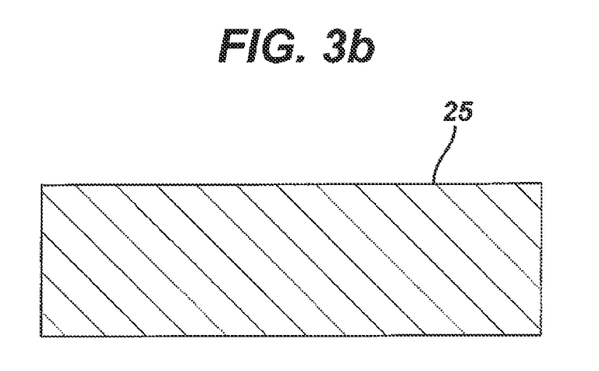
Figure 3C:
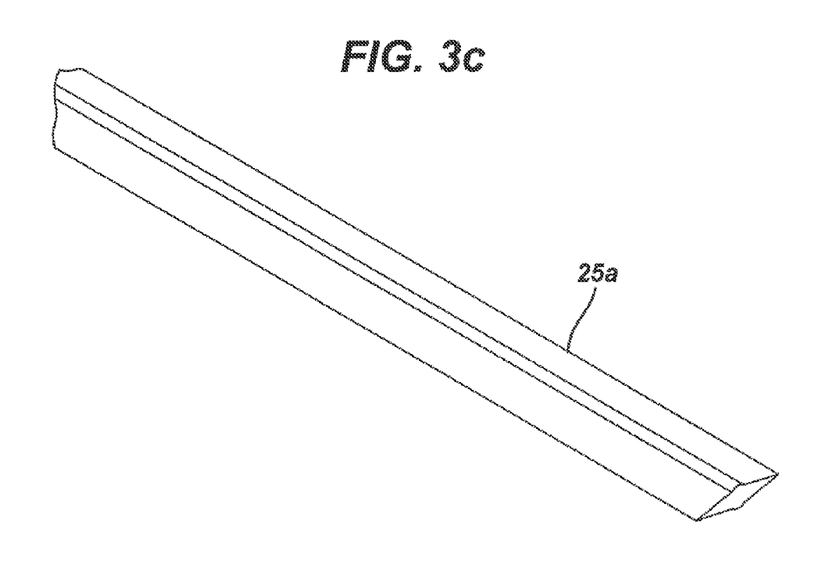
Figure 3D:
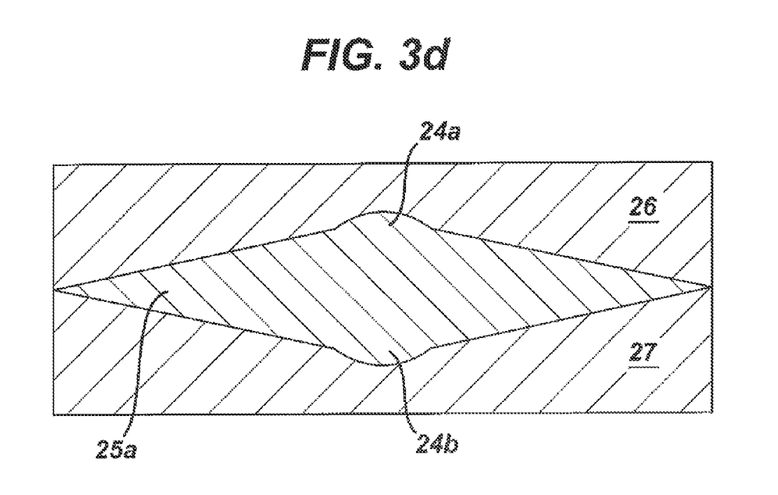
Figure 3E:
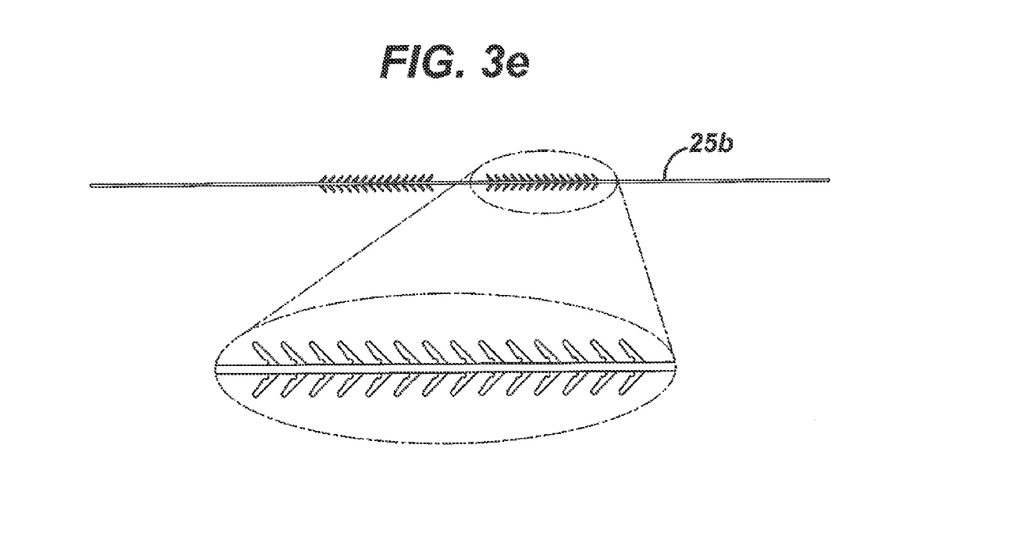
Figure 3F:
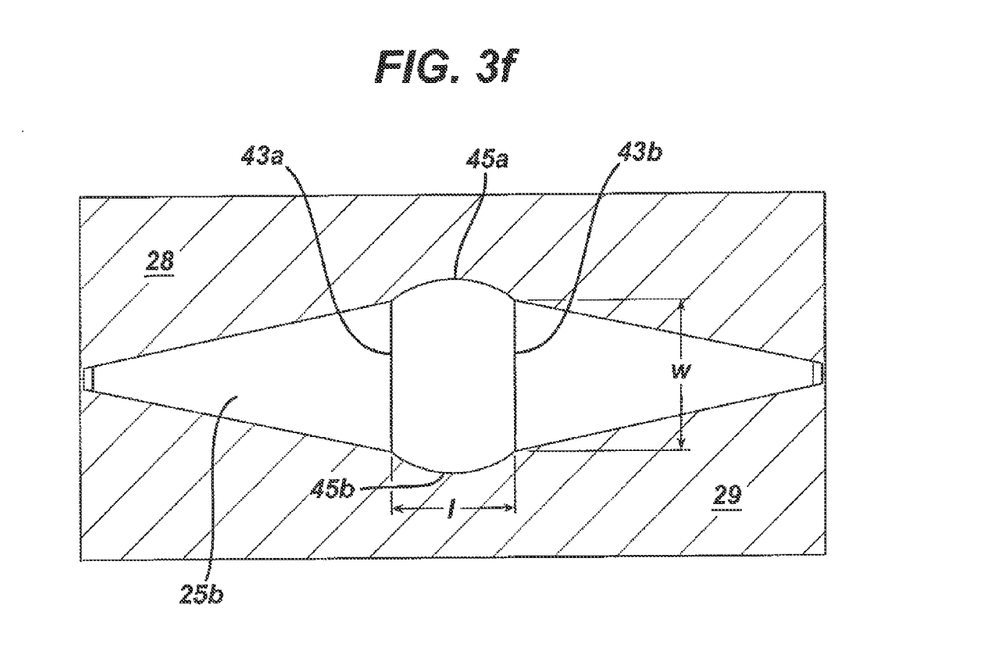

FIGS. 3a-3f illustrate a similar method using multiple dies. A suitable feedstock material 25, such as a polymeric material having a generally rectangular cross section, is shown in FIGS. 3a and 3b. First and second female dies 26, 27 having cavities shaped as shown in FIG. 3d, are press fit together as described above to cause the polymeric material 25 to take the new shape 25a shown in FIGS. 3c and 3d, which has a rhombohedral-like cross-section, with a curved top 24a and bottom 24b portions. A second set of dies 28, 29 is then used to form the material into the final shape 25b as shown in FIGS. 3e and 3f, and to trim off excess material if desired. The use of multiple sets of dies allows for shaping a given feedstock into a more desirable shape from which to form the final device shape. As indicated above, the dies can be compound dies and the dies and/or material may be heated to aid in material flow into the die cavities. The use of multiple sets of dies can serve to limit the amount of heat and/or pressure needed relative to forming with only one set of dies.

Figure 3G:
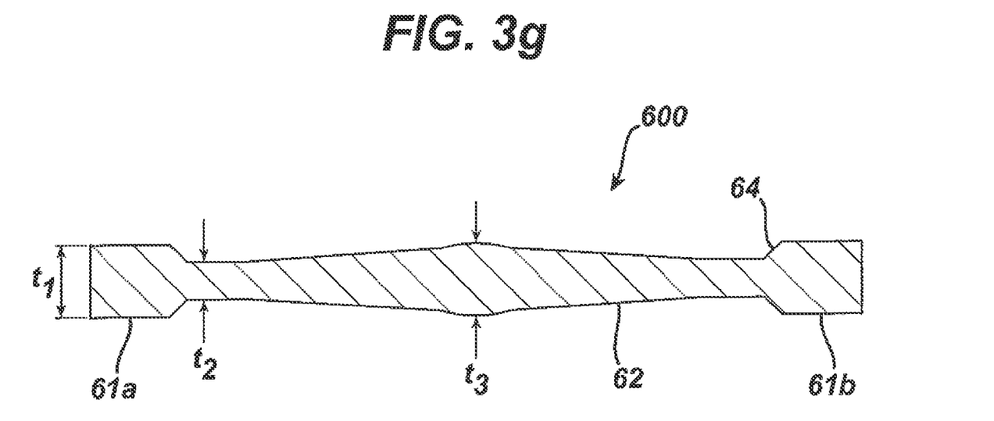
Figure 4A:
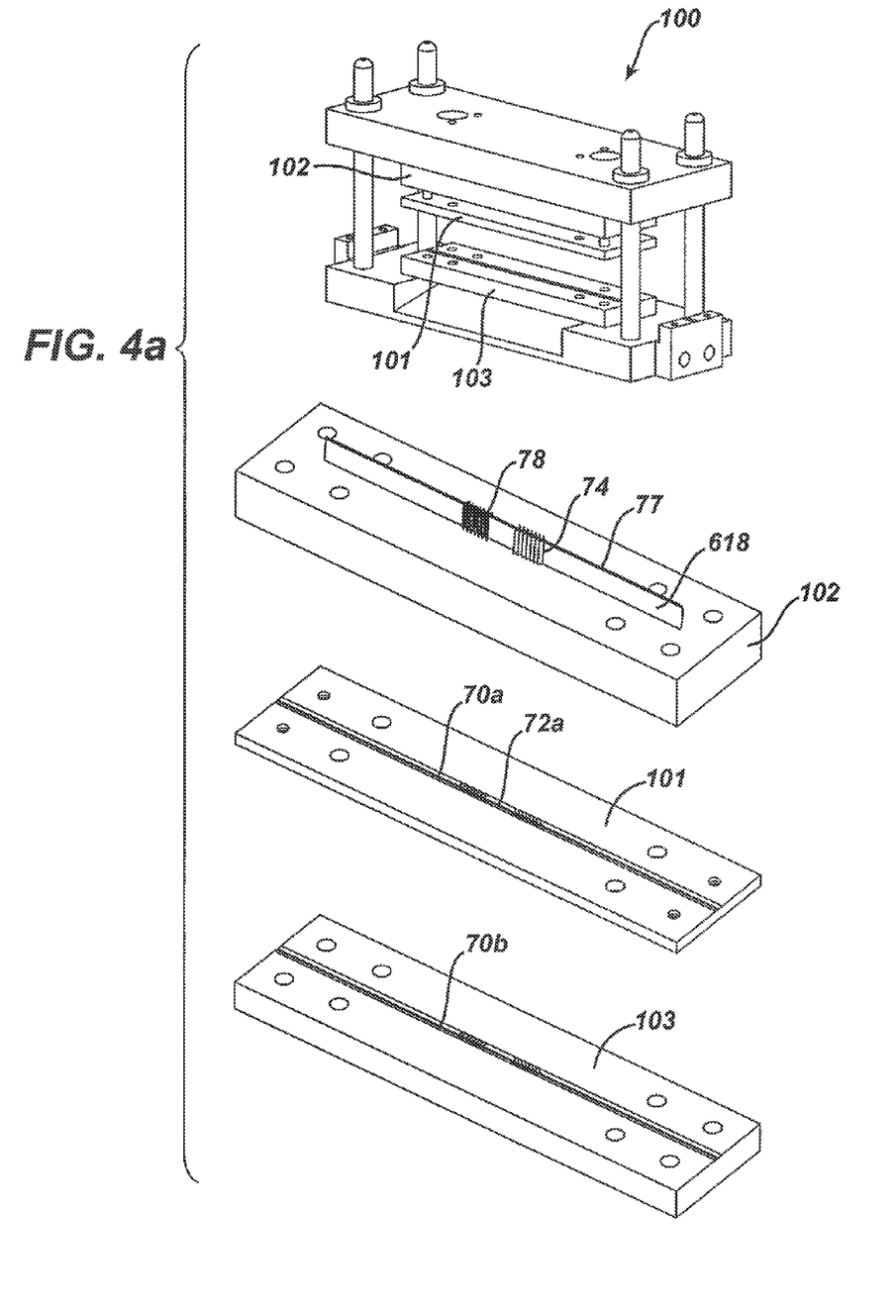
FIGS. 4a-4b illustrate an exemplary compound profile forming/cutting punch and receiver assembly.
Figure 4B:
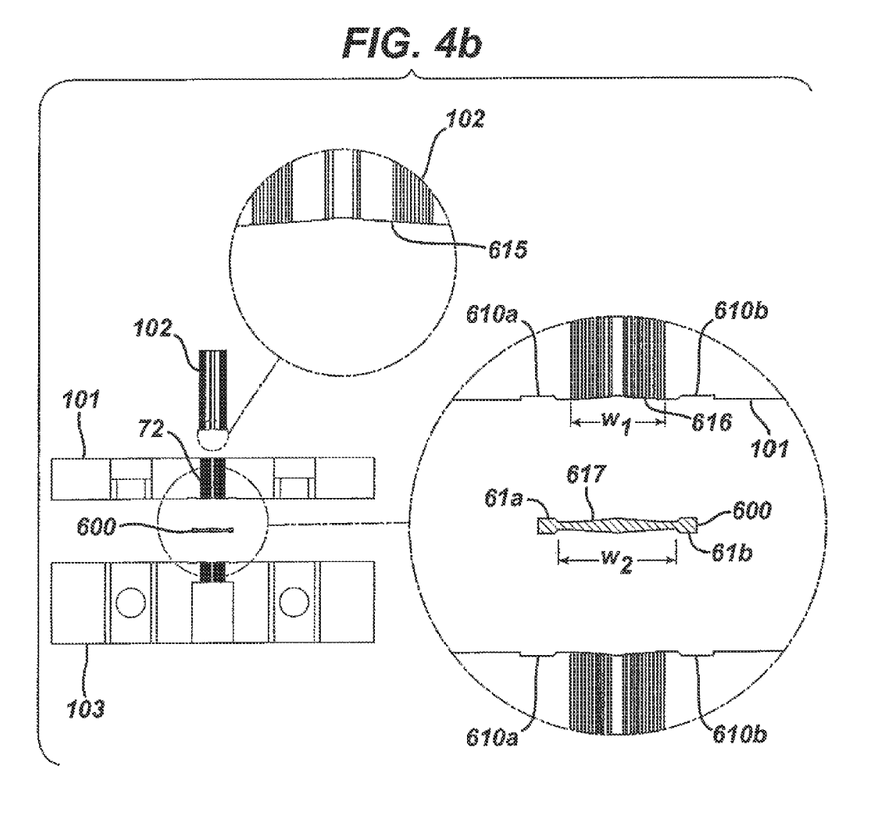

In yet another method, a first set of dies is used to form the pre-form in a similar manner as described above, then, instead of using a second set of dies, a compound profile forming/cutting punch and receiver assembly 100 (as shown in FIGS. 4a and 4b) is subsequently used to profile cut or shear the final shape out of the pre-form. The cross-sectional shape of the pre-form may differ from the cross-sectional shape of the final product. In a preferred embodiment illustrated in FIGS. 3g and 4b, the cross-sectional shape of the pre-form 600 may have more of an "I-beam" shape with a central portion 62 and first and second enlarged distal ends 61a, 61b. By "enlarged distal ends" what is meant is that the distal ends are enlarged as compared to the adjacent section of the central portion, but are not necessarily larger than the entire central portion. For example, as shown in FIG. 3g, the thickness $t_1$ of the enlarged distal ends is greater than the thickness $t_2$ of the adjacent portion of the central portion 62, but is substantially similar to (and may be larger than) the thickness $t_3$ at the center of the central portion. These enlarged ends assist in aligning and holding the pre-form in place within the stripper plate 101 and profile receiver 103 during the subsequent punching step as described below. Providing an angled transition zone 64 (i.e., at a 45 degree angle) can also improve holding and alignment of the pre-form.

The stripper plate 101 and receiver plate 103 similarly have recesses 70a, 70b therein that together, when aligned, form a cavity therebetween. This cavity is capable of receiving the pre-form without exerting any significant forces on the pre-form. Thus, the recesses include portions 610a, 610b (FIG. 4b) that are complementary to the first and second enlarged distal ends 61a, 61b of the pre-form, which aid in aligning the pre-form, and minimizing movement of the pre-form during punching. The stripper plate 101 further includes an opening 72 therethrough designed to receive the punch as will be described further and having a complementary shape.

The profile punch 102 has an outer periphery 74 that is designed to define the outer periphery of the final product, as can best be seen in FIG. 4a. This outer periphery defines both the shape of the central core 77 and tissue grasping elements 78 in the final product. Further, the distal end 615 (FIG. 4b) of the punch has a unique three-dimensional recess 616 therein that is substantially complementary to the top surface 617 of the central portion of the pre-form that is to be punched. This three-dimensional aspect minimizes deformation of the pre-form during the final step as the profile punch 102 punches out the material. Finally, a width $w_1$ of the punch 102 is preferably less than or equal to a width $w_2$ of the central portion of the pre-form so that pre-form can be aligned and held firmly in place at the enlarged distal ends during the final punching step. As is well known in the art, the final punching step is performed by passing the punch element 618 through the complementary opening 72 in the stripper plate, into the pre-form, and preferably further through a complementary shaped opening 72a in the receiver plate, thereby punching out the final product. The advantages of this method are that it may be easier to use a compound profile forming/cutting punch as the final step instead of a forming die, to thereby limit the amount of heat and pressure that is needed. This method may also reduce the amount of flash produced.

Figure 5A:
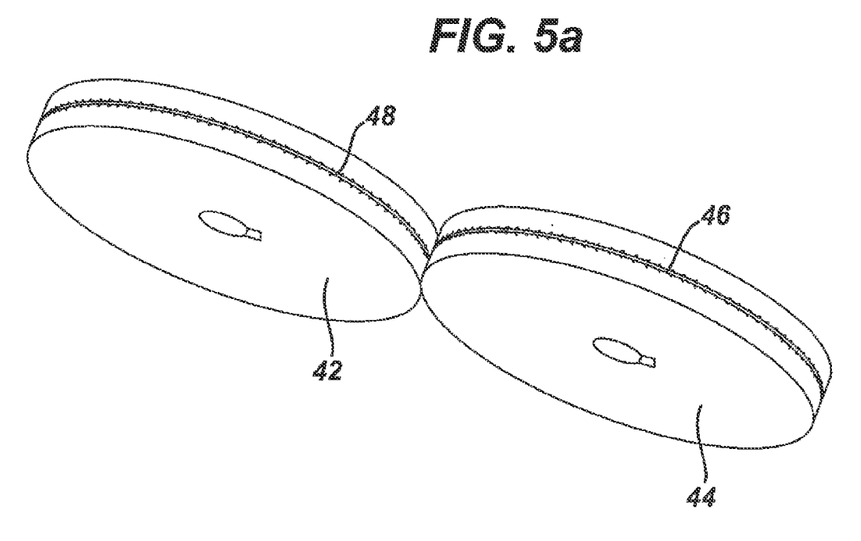
FIGS. 5a and 5b illustrate an exemplary rotary die assembly.
Figure 5B:
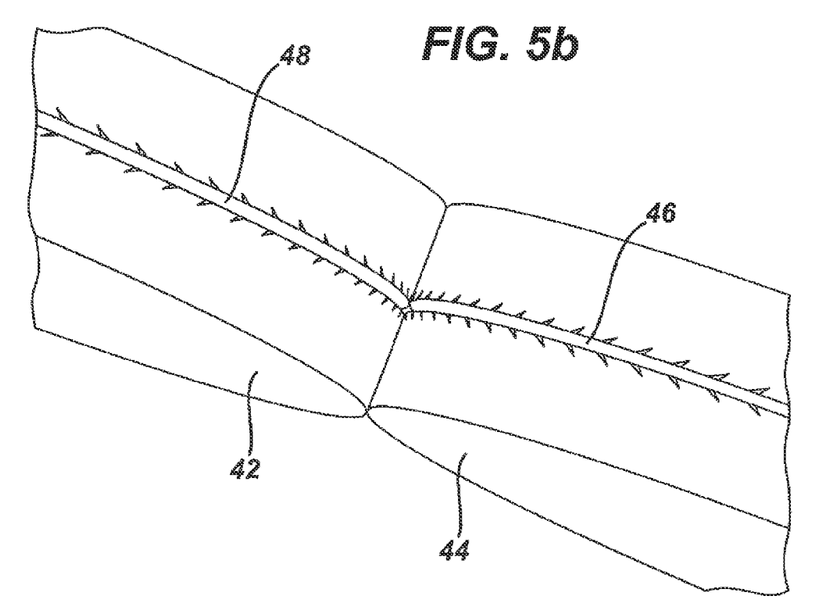

Finally, press-forming or compound profile punching according to the present invention may also be accomplished using a rotary forming or rotary through punch and receiver process, similar to a radial forging-type process, for example, whereby the first 42 and second 44 female dies are circular in shape and have mold recesses or cavities 46, 48 formed in the outer circumference, and rotate in compression against one another to form the material into the desired shape as is illustrated in FIGS. 5a and 5b. This process has the advantage of permitting production of a continuous device, or one having discrete portions with and without tissue holding elements.

Figure 6:
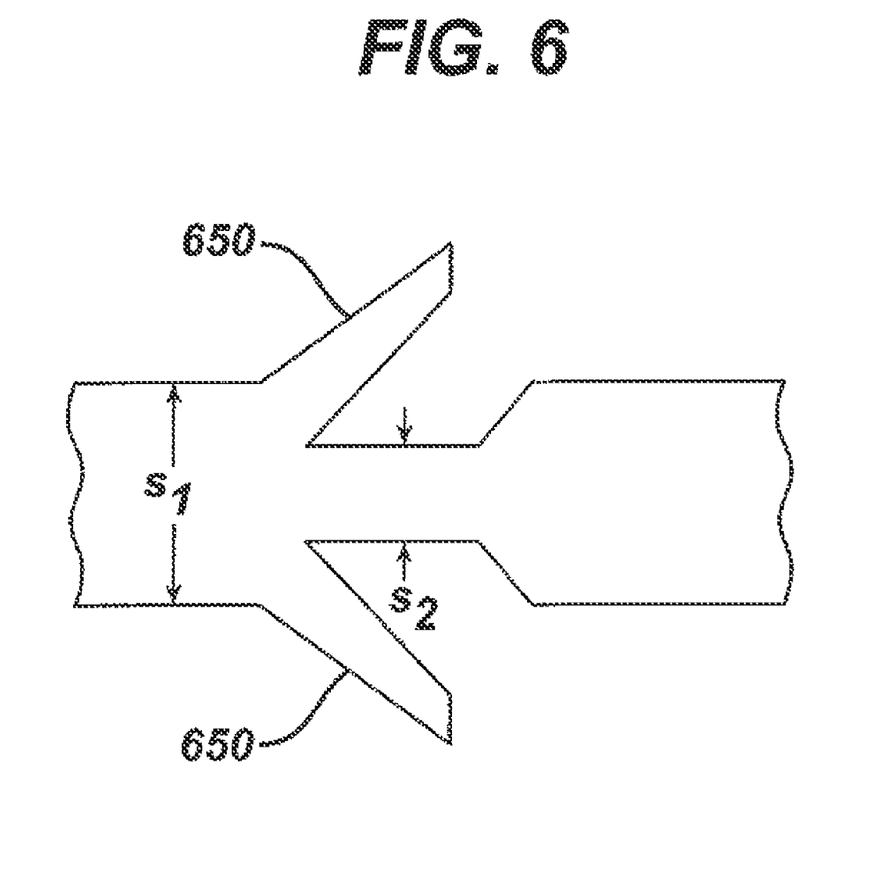
FIG. 6 illustrates an exemplary barbed suture formed by cutting as previously known.

As indicated previously, the above-described methods have distinct advantages over other known methods in that they enable production of tissue holding devices having superior mechanical properties, and also enable production of a tissue holding devices having tissue holding elements of virtually any geometry. With cut barbed sutures, every barb is carved into the suture shaft thereby adversely affecting the holding and tensile strength of the suture at the location of the barb, and providing extensive limitations on the barb geometry and configuration. For example, it is undesirable to place cut barbs 650 opposite one another along the suture shaft, as shown in FIG. 6, since such a configuration doubles the reduction in the suture shaft at that location, as can be seen in comparing the suture shaft diameter $s_1$ to the suture shaft diameter 52 at the location of the barbs. Further, intricate geometries are not possible with cutting, and are limited with injection molding due to the limitations on flowability and the reduction in mechanical properties brought about by this method.

With the above-described methods, there are no barbs cut into the core diameter, but rather there are tissue holding means or elements, such as protrusions, extensions or the like, extending outwardly from an intact core, which may be of any circular or non-circular cross-sectional shape The tissue holding elements can readily be place opposite one another, for example as shown in FIG. 3e, as there is no reduction in the cross-sectional area of the core. Not only is reduction in tensile strength of less concern with press-forming, but it also allows for greater flexibility in suture size selection, since the original suture diameter or cross-section need not be greater than desired to accommodate for any reduction associated with cutting into the suture core or shaft.

Figure 7:
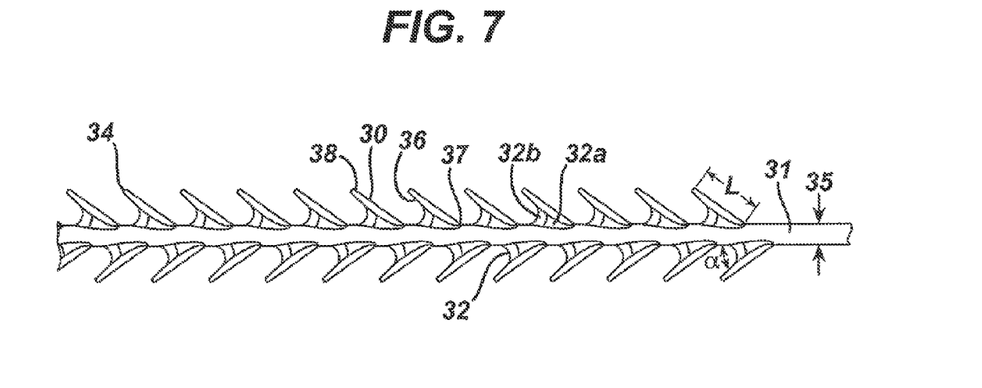
Figure 8:
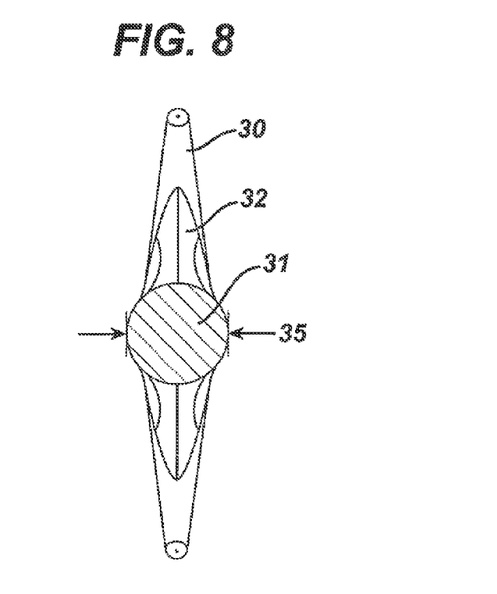

Another tissue holding device according to the present invention is illustrated in FIGS. 7-8. Multiple tissue holding elements 30 extend outwardly from suture shaft 31, with each element further including a web-like portion 32 extending between the inner side 36 of the tissue holding element and the suture shaft. Preferably, this web-like portion is thinner than the main tissue holding element 30. The web-like portion 32 allows the tissue holding elements to fold against the suture shaft during insertion into tissue or other material, but also serves to reinforce the strength of the tissue holding element and provide resistance against peeling back of the tissue holding element. This can greatly increase the holding strength for a given suture diameter and configuration of the tissue holding element 30. Each tissue holding element may also be configured with a radiused tip 34 to reduce tissue irritation and the like while still maintaining holding ability. Further, the web-like portion 32 may be continuous or non-continuous. For example, a section 32a nearest the base may be eliminated leaving only a strip 32b of the web-like portion between the tissue holding element and the shaft or core 31.

In the configuration described above, with or without the web-like portions, the suture may have a core diameter 35 of approximately 0.005-0.035 inches, and preferably 0.014 inches. The central core of the device may also be of any other suitable cross-section, such as the exemplary embodiment illustrated in FIG. 3f. In this embodiment, opposing upper and lower sides 45a, 45b are curved, whereas opposing lateral sides 43a, 43b are substantially flat or straight. The width w and length l are each preferably in the range of 0.006-0.020 inches, and more preferably approximately 0.012 inches. For purposes of this disclosure, the term "outermost dimension" refers to the largest dimension that can be measured across the cross-section of the core. The length L (see FIG. 7) of the tissue holding elements may be 0.010-0.20 inches, and preferably approximately 0.030-0.065 inches. Although the tissue holding elements 30 illustrated in FIG. 7 are substantially conical in shape, any other suitable configuration may also be used, such as pyramidal, cylindrical etc. In a preferred embodiment, the base 37 or proximal end of the main tissue holding element 30 has a diameter of approximately 0.006-0.05 inches, and a tip 38 or distal end has a diameter of approximately 0.001-0.006 inches. Further, although the illustrated embodiment shows tissue holding elements at approximately 180 degrees spacing about the circumference of the suture shaft (opposite sides), any other suitable spacing (i.e., 120 degree spacing) may also be achieved with the methods described herein. Tissue holding element angle $\alpha$ may be any suitable angle between 1 and 90 degrees, with a currently preferred embodiment being approximately 52 degrees. Finally, the spacing between successive barbs on a given side of the suture may be approximately 0.01-0.1 inches, and preferably approximately 0.030 inches.

The tissue holding devices described herein may be formed of any material suitable for press-forming and suitable for implantation into the body. A preferred material is polypropylene or polyvinylidene fluoride (PVDF). Other suitable polymeric materials include absorbable materials such as polydioxanone, polyglactin, polyglycolic acid, copolymers of glycolide and lactide, polyoxaesters, poliglecaprone etc., or non-absorbable materials such as polypropylene, polyethylene, polyvinylidene fluoride (PVDF), polyesters, polyethylene terephthalate, glycol-modified polyethylene terephthalate, polytetrafluoroethylene, fluoropolymers, nylons etc. and the like, or copolymers of combinations thereof, including combinations of absorbable and non-absorbable materials. In addition, metals or ceramics may be suitable for certain applications, such as instances where specific strength or corrosion resistance is necessary. Yet another embodiment allows for the addition of fibers, such as glass fibers, to a polymeric material to provide reinforcement and subsequent increased mechanical properties. Finally, shape memory metals or polymers could be used that, for example, maintain the tissue holding elements in a collapsed position during normal room temperatures, but that return to an uncollapsed position when exposed to body temperature.

Figure 9A:
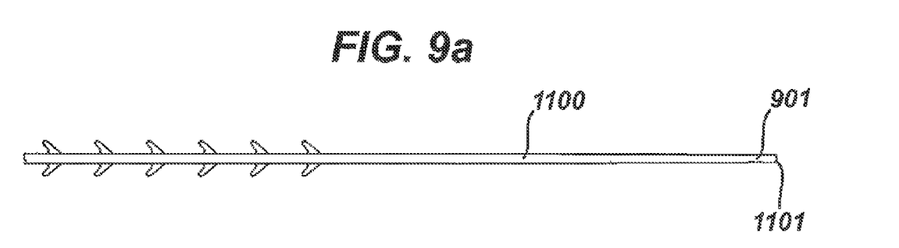
Figure 9B:
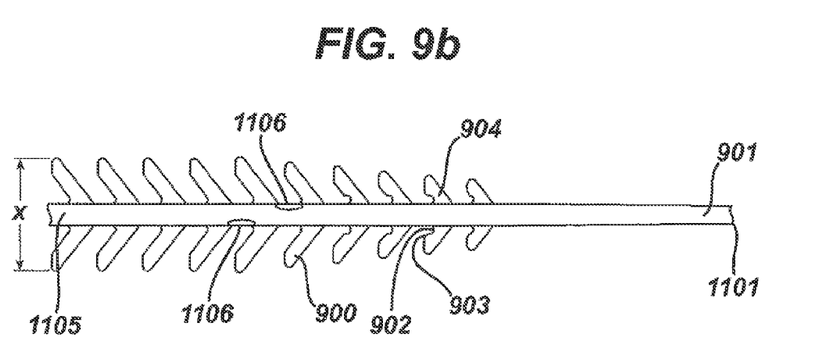

Referring now to FIGS. 9a and 9b, the tissue holding elements 900 may be configured to better facilitate folding against the suture shaft 901 during insertion by providing a notch, recess or the like 902 on the inner side 903 thereof, preferably in proximity to the proximal end 904 of the tissue holding element as shown. The recessed area may decrease tissue trauma by allowing the tissue holding elements to "fold" during insertion. Further, the tissue holding elements 900 may be formed with a reinforced or wider proximal end as shown to provide added strength and to help prevent peeling back of the tissue holding element.

The devices of the present invention may also incorporate a variety of additional features such as a tapered leading end 1100 having a smaller cross-section at the distal end 1101 to lessen resistance and tissue trauma during insertion. The device of FIG. 9b further has a gradually increasing outer dimension x (distance between distal tips of opposing or nearly opposing tissue holding elements) along the length or a portion of the length from the leading end 1101 toward the distal end 1105. This feature similarly serves to facilitate insertion of the device into tissue. In addition, the device of FIG. 9b may include one or more recesses 1106 behind the tissue holding elements designed and positioned such that the tissue holding element fold backward at least partially into the recess when the device is drawn through tissue, which serves to reduce the outer cross-sectional profile and therefore facilitate insertion, minimize tissue trauma, and minimize the channel formed in the tissue.

Figure 10:
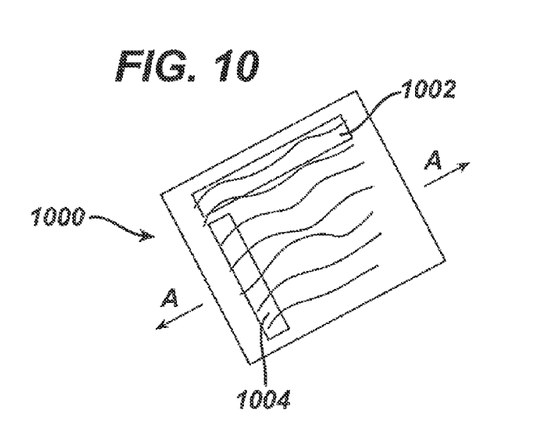
FIG. 10 is an exemplary illustration of molecular orientation and optimization thereof.

Another advantage of devices formed according to the methods described above is that such devices can readily take advantage of molecular orientation and the properties that such orientation imparts to the final product. For example, the feedstock material can be provided in a sheet 1000 such as that shown in FIG. 10. With a polymeric material, the sheet may be constructed so as to have a particular molecular orientation, such as one that is primarily in the direction of arrow A. If a high tensile strength is desired in the end product, the feedstock may be cut out of the sheet in that same direction, such as is shown by reference numeral 1002. If the holding strength of the tissue grasping devices is the most important, the feedstock could be cut as shown by reference numeral 1004.

As is apparent from the description above, the use of press-forming or compound profile punching to form tissue holding devices is highly advantageous in that it can be used to achieve virtually any three-dimensional configuration without regard to intricate geometries of the tissue holding elements, without regard to positioning of the tissue holding elements, without concern as to reducing the tensile strength of the suture, and without adversely affecting the structural integrity of the original feedstock material.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A method for forming a tissue holding device having a predetermined shape suitable for use in surgical applications, comprising:
    providing a polymeric feedstock material;
    using a first set of dies, press forming the polymeric feedstock material into a pre-form having a length and a width, wherein the width is defined by a central portion and first and second enlarged distal ends;
    providing a receiver plate and a stripper plate each having a top surface with a recess formed therein having a three-dimensional shape such that, when the recesses are aligned and facing one another, a cavity is formed therebetween capable of receiving therein the pre-form and having a substantially complementary shape as that of the pre-form, including the central portion and enlarged distal ends thereof, the stripper plate further having a opening therethrough for receiving a punch;
    aligning the receiver and stripper plates and placing the pre-form in the cavity formed therebetween;
    providing a punch having a punch element having an outer periphery substantially identical to an outer periphery of the predetermined shape of the tissue holding device, and having a three dimensional surface contour substantially complementary to a top surface of a portion of the pre-form to be punched;
    pressing the punch element through the stripper plate and into the pre-form to thereby create the tissue holding device of the predetermined shape, wherein the punch element presses into only the central portion of the pre-form and not the enlarged distal ends of the pre-form;
    wherein the predetermined shape of the tissue holding device includes a core extending along a length thereof and having an outermost dimension of less than or equal to 0.03 inches, and a plurality of tissue holding elements extending outwardly therefrom along at least a portion of the length.

2. The method according to claim 1, wherein the plurality of tissue holding elements have a length less than or equal to 0.2 inches.

3. The method according to claim 1, wherein the plurality of tissue holding elements include at least first and second tissue holding elements positioned opposite one another at substantially the same location along the length of the core.

4. The method according to claim 1, wherein the plurality of tissue holding elements extend outwardly from the core at an angle, and wherein the tissue holding device further includes a web-like portion extending between an inner side of the tissue holding elements and the core, wherein the web-like portion is thinner than the tissue holding element.

5. The method according to claim 1, wherein the core of the tissue holding device has a cross-sectional shape comprising opposing upper and lower outwardly curved sides and opposing first and second substantially flat lateral sides.

6. The method according to claim 5, wherein the plurality of tissue holding elements extend outwardly from the first and/or second lateral sides.

7. The method according to claim 5, wherein the tissue holding elements have a length less than or equal to 0.2 inches.

8. The method according to claim 1, wherein the core has a substantially uniform cross-section along its length.

9. The method according to claim 1, wherein the core increases in cross-section along at least a portion of its length.

10. The method according to claim 1, wherein at least one of the plurality of tissue holding elements has an inner side having a recess therein.

11. The method according to claim 1, wherein a length of the tissue grasping elements increases along at least a portion of the length of the tissue holding device.

12. The method according to claim 1, wherein the first set of dies are circular in shape, each having a recess in an outer circumference thereof.

\* \* \* \* \*